(12) United States Patent
Robles et al.

(10) Patent No.: US 7,608,760 B2
(45) Date of Patent: Oct. 27, 2009

(54) BROWN MUSHROOMS FOR COMMERCIAL PRODUCTION

(75) Inventors: Christopher William Robles, Aptos, CA (US); Stephen Christopher Lodder, Aptos, CA (US)

(73) Assignee: Amycel Inc., Watsonville, CA (US)

( * ) Notice: Subject to any disclaimer, the term of this patent is extended or adjusted under 35 U.S.C. 154(b) by 597 days.

(21) Appl. No.: 11/267,043

(22) Filed: Nov. 3, 2005

(65) Prior Publication Data

US 2007/0033679 A1 Feb. 8, 2007

Related U.S. Application Data

(60) Provisional application No. 60/705,862, filed on Aug. 4, 2005.

(51) Int. Cl.
*A01H 15/00* (2006.01)
*A01G 1/04* (2006.01)

(52) U.S. Cl. .......................... 800/297; Plt./394; 47/1.1
(58) Field of Classification Search .................. 800/297
See application file for complete search history.

(56) References Cited

U.S. PATENT DOCUMENTS

| 4,996,390 | A |   | 2/1991  | Dahlberg       |         |
|-----------|---|---|---------|----------------|---------|
| PP7,636   | P | * | 8/1991  | Spear et al.   | Plt./394 |
| 5,304,721 | A | * | 4/1994  | Kerrigan et al.| 800/260 |
| 5,832,659 | A |   | 11/1998 | Loftus et al.  |         |
| 2004/0144020 | A1 |   | 7/2004 | Kerrigan et al.|         |

OTHER PUBLICATIONS

ATCC webpage. <www.atcc.org/common/catalog/numSearch/numResults.cfm> printed Nov. 6, 2007.*
Callac, P., "Morphological, Genetic, and Interfertility Analyses Reveal a Novel, Tetrasporic Variety of *Agaricus bisporus* from the Sonoran Desert of California," Mycologia, 85(5), pp. 834-851, 1993.
Castle et al., "Crosses among Homokaryons from Commercial and Wild-Collected Strains of the Mushroom *Agaricus brunnescens* (—A. *bisporus*)," Appl. Environ. Microbiol., 54(7), 1643-1648, Jul. 1988.
Castle et al., "Restriction Fragment Length Polymorphisms in the Mushrooms *Agaricus brunnescens* and *Agaricus bitorquis*," Appl. Environ. Microbiol.,, 53(4), pp. 816-822, Apr. 1987.
Downie et al., "Basic Statistical Methods," Harper & Brothers, New York, 1959 (see especially chapter 12, pp. 123-139, Testing Difference Between Means.).

Elliot, T.J., "The Genetics and Breeding of Species of *Agaricus*," in Flegg et al., eds, The Biology and Technology of the Cultivated Mushroom. John Wiley & Sons, Ltd., pp. 111-139, 1985.
Evans, H.J., "Nuclear Behavior in the Cultivated Mushrooms," Chromosoma (Berl.) 10, pp. 115-135, 1989.
Fritsche, G., "*Breeding Agaricus bisporus* at the Mushroom Experimental Station, Horst," The Mushroom Journal, 122, pp. 49-53, 1983.
Fritsche, G., "Personal View on Mushroom Breeding From 1957-1991," Genetics and breeding of *Agaricus*, Proceedings from the First International Seminar on Mushroom Science, Mushroom Experimental Station, Horst, the Netherlands, May 14-17, 1991.
Kerrigan et al., "Strategies for the Efficient Recovery of *Agaricus bisporus* Homokaryons," Mycologia, 84(4), pp. 575-579, 1992.
Kerrigan, R.W., Development Potential of Wild *Agaricus bisporus*, 53, pp. 14-23, 2005.
Khush, et al., "DNA Amplification Polymophisms of the Cultivated Mushroom *Agaricus bisporus*," Appl. Environ. Microbiol., 58(9), pp. 2971-2977, Sep. 1992.
Loftus, et al., "DNA polymorphisms in commercial and wild strains of the cultivated mushroom, *Agaricus bisporus*," Theor. Appl. Genet. 76, pp. 712-718, 1988.
Loftus, et al., "Use of a SCAR marker for cap color in *Agaricus bisporus* breeding programs," Science and Cultivation of Edible Fungi, Van Griensven (ed.), pp. 201-205, 2000.
May et al., "Confirmation of crosses between Lines of *Agaricus brunnescens* by Isozyme Analysis," Exp. Mycology, vol. 6. pp. 283-292, 1982.
Mueller et al., "AFLP genotyping and fingerprinting," Trens Ecol Evol. vol. 14(10), pp. 389-394, Oct. 1989.
Paran et al., "Development of reliable PCR-based markers linked to downy mildew and resistance genes in lettuce," Theor. Appl. Genet., 85, p. 965-993, 1993.
Sonnenberg et al., "An Efficient Protoplasting/Regeneration System for *Agaricus bisporus* and *Agaricus bitorquis*," Curr. Microbiol., vol. 17, pp. 285-291, 1988.
Summerbell et al., "Inheritance of Restriction Fragment Length Polymorphisms in *Agaricus brunnescens*," Genetics, 123, pp. 293-300, Oct. 1989.
Williams et al., "DNA polymorphisms amplified by arbitrary primers are useful as genetic markers," Nucleic Acids Research, vol. 18(22), pp. 6531-6535, 1990.
Xu et al., "localization of the mating type gene in *Agaricus bisporus*," Appl. Environm. Microbiol., vol. 59(9), pp. 3044-3049, Sep. 1993.

* cited by examiner

*Primary Examiner*—Anne Marie Grunberg
*Assistant Examiner*—Keith O. Robinson
(74) *Attorney, Agent, or Firm*—Cooley Godward Kronish LLP

(57) ABSTRACT

Hybrid *Agaricus bisporus* mushroom strains having one or more genetic characteristics of a wild mushroom strain deposited under ATCC accession No. PTA-6903 or a progeny thereof and having specified physical and genetic characteristics are disclosed along with methods of producing brown mushrooms for commercial use.

23 Claims, No Drawings

BROWN MUSHROOMS FOR COMMERCIAL PRODUCTION

CROSS-REFERENCE TO RELATED APPLICATION

This application is claims the benefit of provisional U.S. application Ser. No. 60/705,862, having the same title and inventors, which was filed on Aug. 4, 2005, and is herein incorporated by reference.

BACKGROUND OF THE INVENTION

The cultivated white button variety of *Agaricus bisporus*, known as *A. bisporus* (Lange) Imbach (syn. *A. brunnescens* Peck), is the predominant mushroom species in cultivation in the world today. After many years in which commercial mushroom sales in the United States were restricted primarily to white button *A. bisporus* mushrooms, there has been a recent trend toward increased sales of brown *A. bisporus* mushrooms of various types and other so-called exotic strains (species other then *A. bisporus*), as such mushrooms have increased flavor relative to the bland taste of white button mushrooms. However, many of these more flavorful and exotic tasting mushrooms are difficult to produce commercially or can only be collected in the wild. For example, Enoki mushrooms, also called enokitake (*Flammulina velutipes*), originated in Japan where they were gathered in the wild, although in the United States they are cultivated on live or dead tree trunks, tree roots, or branches that have been covered with soil. Shiitake mushrooms (*Lentinus edodus*), also known as Japanese black forest mushrooms, have been commercially cultivated and are widely available either fresh or dried in supermarkets as well as in Asian markets, although their commercial production is more difficult than that of *A. bisporus*, which grows in easily harvested beds. Originally harvested from hardwood trees in their native country for at least two thousand years, shiitakes are often cultivated on artificial logs made from sawdust. Morels (*Morchella esculenta*) are gathered in the wild in wooded areas in the spring. Scandinavians refer to morels as "truffles of the north." Chanterelles (*Cantharellus cibarius*) grow in the wild in the Pacific Northwest in forests with pine trees and deciduous trees. Truffles (*Tuber aestivum*), perhaps the most famous fungus in the world and certainly the most expensive, are fungi that grow underground in wooded areas. They have never been successfully cultivated and are a challenge to forage in the wild. They can only be located by dogs or pigs that have been are specially trained to recognize the scent of the truffle. Black truffles from France, known as Perigord, are best known for flavoring pate de foie gras. White truffles from the Alba region of Italy are also available.

As should be apparent from the description above, commercial production of many exotic strains is difficult. This difficulty in commercial production has been overcome in part by developing strains of *A. bisporus* with similar colors, appearances, and flavors that can be used as a replacement for the exotic or wild mushroom strains described above. These "exotic" *A. bisporus* strains can be appreciated by discriminating consumers while still being capable of production in the standard commercial processes developed for *A. bisporus* production. Crimini (or cremini) is an *Agaricus bisporus* strain, similar to the familiar white *A. bisporus* mushroom strains found in most grocery stores, but it has a brownish color and is denser in texture with a pronounced earthy flavor. Portabellas (also spelled portobellos), which have only been widely available since the 1980s, are sometime thought of as an Italian strain of mushrooms but are actually large criminis that have been allowed to grow for longer periods of time. Because of their longer growth time, portabellas have a distinctly pungent, earthy flavor and fleshy texture and have seen increased use in recent years, often as a substitute for meat in vegetarian dishes, in addition to being used in side dishes or sauces for their own distinctive flavor.

Both white and brown strains of *Agaricus bisporus*—being varieties of the same species—have the same complex genetics and unusual biology. *A. bisporus* produces predominantly two spores per basidium, in contrast to most basidiomycetes fungi, which produce four spores per basidium. With four spores per basidium, each spore receives one of the four haploid nuclei produced by meiosis and germinates to form a haploid mycelium (a homokaryon). In *A. bisporus* each of the two spores typically receive two post meiotic nuclei referred to as "a" and "b". There is good evidence (Evans H. J., in Chromosoma 10 115-135 (1959)); Summerbell, R. C., Castle, A. J., Horgen, P. A. & Anderson, J. B. in Genetics 123 293-300(1988)) that *A. bisporus* spores derived from two-spored basidia preferentially contain nuclei of complementary mating type. These spores germinate to produce diploid, self-fertile mycelium, known as heterokaryons, which contain the two nuclei a and b. This self fertile heterokaryon can, under the correct environmental conditions, undergo several fruiting cycles commonly referred to as "breaks." A crop of mushrooms comprises the total yield from several successive breaks.

In addition to self-fertile spores, viable non-self fertile spores are produced at the rate of 1 to 20%. These homokaryotic spores arise from aberrant three- and four-spored basidia. The homokaryotic mycelium derived from these spores can be used for the controlled crossing that is the foundation of *A. bisporus* breeding. A traditional *Agaricus* breeding program utilizes the fact that homokaryons grow more slowly than heterokaryons. This permits the screening of large populations of spores for suitable parents, which can then be used in controlled crosses (Kerrigan, R. W., Baller, L. M., Horgen, P. A. & Anderson, J. B), in Mycologia 84 575-579(1992). This approach was used successfully by G. Fritsche (described in The Mushroom Journal 122 49-53 (1983) and in Genetics and Breeding of *Agaricus*, Chapter 1, 3-20, Pudoc (1991)) to develop the strains U1 and U3. Since their release in 1983, these strains have dominated the industry, either as U1, as U3, or as derivatives sold worldwide by numerous spawn companies (Castle, A. J., Horgen, P. A. & Anderson, J. B., in Applied and Environmental Microbiology 53 816-822 (1987); Loftus, M. G., Moore, D. & Elliott, T. J., in Theoretical and Applied Genetics 76 712-718 (1988)).

These U1 and U3 hybrid strans and their typical progeny are the white button mushrooms commonly found in grocery stores. Brown *Agaricus bisporus* mushroom strains of the portabella type that are currently available for commercial use include, but are not limited to, Sylvan SB65, Lambert 800, Lambert 801, Sylvan 295, Amycel 2400, and Amycel Bella. These are genetically related strains of a general class often referred to as "old fashioned browns" in the industry. Any improvement in color, appearance, flavor, and/or production values of these strains would be commercially advantageous.

Recent developments in mushroom genetics have allowed new strains of mushrooms to be developed via crossing, although there is still too much complexity in the genetic picture for crossing of untested strains to occur in a predictable manner. Most of the initial crosses have either the characteristics of the parents and thus do not represent improvements or have unexpected characteristics that are less desirable than those of the parent strains. However, once a desirable strain has been identified and developed, cell cultivation techniques allow commercial production of genetic clones via mushroom spawn, and the identification of genetic markers in the new strain allows its desirable characteristics to be followed into its progeny and used to select desirable strains from future crossings. At least one new mushroom strain has been the subject of a U.S. plant patent (No. Plant 7,636), while utility patents have issued on specific strains with improved characteristics (e.g., U.S. Pat. Nos. 4,996,390, 5,304,721, and 5,832,659).

All brown strains commonly available for sale in the U.S. are genetically identical, except the hybrid Sylvan 600 (syn. X618). There are a number of advantages for introducing greater genetic diversity into commercial brown mushroom production. The genetic homogeneity of the commercial brown crosses is especially problematic if a novel crop pathogen emerges which causes devastating crop losses. Since nearly all of the commercial brown strains are identical, they would be equally affected.

Additionally, cap color is one of them most important economic physical characteristic of *A. bisporus* strains. Currently available brown strains of *A. bisporus* all have generally the same (more or less) brown tone, and the development of brown strains that have a darker color would be economically advantageous.

Accordingly, there is a need for new mushroom strains having genetic diversity as well as improved appearance, flavor, and/or production characteristics that that exceed those of existing portabella mushrooms. By the introduction of wild mushroom germ plasma into commercial mushroom strains, we have a developed a novel breeding pedigree. The products of our pedigree give brown mushrooms of the portabella and crimini varieties having good flavor and appearance as well as having excellent production values.

BRIEF SUMMARY OF THE INVENTION

It is an object of the invention to provide brown varieties of *Agaricus bisporus* mushroom with improved commercial characteristics relative to existing brown commercial mushrooms. Specifically, it is an object of the invention to provide mushrooms that have one or more (most preferably all) of the following characteristics (relative to brown *Agaricus bisporus* now being marketed):

Increased productivity

Darker, more attractive cap color

Thicker cap

Non-compatibility with existing strains or antagonism with existing strains (genetic disease barrier).

These and other objects of the invention have been accomplished by providing a hybrid *Agaricus bisporus* mushroom strain obtained by crossing a mushroom of wild strain AA-0096 or a progeny thereof with a second *Agaricus bisporus* strain, wherein the mushroom of the invention (1) has (a) at least one genetic characteristic of wild strain AA-0096 not present in the second *Agaricus bisporus* strain and (b) at least one genetic characteristic of the second *Agaricus bisporus* strain not present in wild strain AA-0096 and (2) either (a) has at least one physical characteristic selected from the group consisting of cap color, cap thickness, and productivity that is statistically better than the corresponding physical characteristic of comparison strain Amycel 2400 or (b) is genetically non-compatible with comparison strain Amycel 2400.

DETAILED DESCRIPTION OF THE INVENTION

The present invention arose from a breeding program that crossed mushrooms derived from commercial *Agaricus bisporus* strains with wild mushroom strains. The specific wild mushroom strain that was eventually found to provide the desired genetic characteristics is known as AA-0096. This wild strain was previously described in the scientific literature because of its unique genetics. Strain AA-0096 is also known as BP-1 and ARP-023 and is available from the American Type Culture Collection (ATCC) under accession number 76562 as a non-patent deposit. This strain has been re-deposited by the current inventors under the Budapest Treaty governing the deposit of organisms for patent purposes at the American Type Culture Collection, Rockville, Md., USA, under ATCC accession No. PTA-6903 (inventors' identification AA-0096, deposited on Aug. 3, 2005). Specific progeny strains obtained by crossing AA-0096 with other *A. bisporus* strains can be selected to have at least one (preferably all four) of the improved characteristics described herein by using the procedures described herein. Examples of such strains include the BR06 strain that is described in more detail below.

As a result of the ATCC deposit recited above (and other deposits described below relating to preferred embodiments), anyone can practice the current invention using standard methods of mushroom breeding and/or production, using either the already deposited strains or (in the future) commercial mushrooms derived from strain AA-0096 that have reached the marketplace, as processes for cloning mushrooms from mushrooms available at the retail level (as in grocery stores) are well known. Specific cloning processes (which produce genetically identical crops of mushrooms) and crossing processes (which produce non-genetically identical progeny) that can be used in the practice of the invention are described in this application. For example, the genetic characteristics of preferred strain BR06 can be transmitted to cloned mushrooms without change, or new progeny of the original wild strain having the commercially desirable characteristics recited herein (referred to as "commercially acceptable AA-0096 derivatives") can be prepared using the general breeding techniques described here, and further progeny (as well as later crosses derived from these progeny) can be selected for the recited commercially desirable characteristics.

Methods for the production of mushroom strains, either as direct progeny (clones) of a given strain or as hybrid progeny by crossing with a second strain, are well known. See, for example, U.S. Pat. No. 5,304,721, entitled "Method for the Production of High Proportions of Homokaryons in Breeding Stock of the Mushroom *Agaricus Bisporus*" and U.S. Pat. No. 4,996,390, entitled "Novel Interspecific Mushroom Strains," as well as numerous publications in the scientific literature, including Sonnenberg et al., "An Efficient Protoplasting/Regeneration System for *Agaricus bisporus* and *Agaricus bitorquis*," Curr. Microbiol., 17:285-291 (1988); May et al., "Confirmation of Crosses Between Lines of *Agaricus brunnescens* by Isozyme Analysis," Exp. Mycology, 6:283-292 (1982); Herbraud et al., "Protoplast Production and Regeneration from Mycorrhizal Fungi and Their Use for Isolation and Mutants," Can. J. Microbiol., 34:157-161 (1988); Loftus et al., "DNA Polymorphisms in Commercial and Wild Strains of the Cultivated Mushroom, *Agaricus bisporus*," Theor. Appl. Genet., 76:712-718 (1988); Elliott, "The Genetics and Breeding of Species of *Agaricus*," in Flegg et al., eds, The Biology and Technology of the Cultivated Mushroom, John Wiley and Sons, 1985, pp. 111-139; Castle et al., "Crosses Among Homokaryons from Commercial and Wild-Collected Strains of the Mushroom *Agaricus brunnescens* (=*A. bisporus*)," Appl. Environ. Microbiol., 54:1643-1648 (1988); and Castle et al., "Restriction Fragment Length Polymorphism in the Mushrooms *Agaricus brunnescens* and *Agaricus bitorquis*," Appl. Environ. Microbiol., 53:816-822 (1987).

These are merely a few of the numerous publications in the field of mushroom strain production and recognition, and many equivalent publications exist for those who are less familiar with this area of technology and would like to pursue additional background material (see, for example, the publications cited in each of the patent or other publications listed above). Now that the genetic material of the newly developed strains has been placed in the hands of those skilled in the art of mushroom production by the present invention, one can practice the invention (including the development of progeny strains from the parent deposited strains) simply by using standard mushroom breeding techniques. In particular, progeny of the deposited strains can be prepared simply by following the procedures shown in detail in the Examples that follow.

Numerous wild mushrooms strains were tested to determine whether wild strains of mushroom could be used to improve commercial strains of brown *A. bisporus* mushrooms, most without success in producing any commercially viable varieties. Wild heterokaryon AA-0096 had been chosen as one of the test strains because it is very different genetically from common commercial mushroom cultivars (Callac, P., Biliette, C., Imbemon, M. & Kerrigan, R. W., in Mycologia 85 835-851 (1993)). These genetic differences, however, made it unpredictable as to what results would be obtained by using this strain in attempts to produce commercially viable brown strains. For example, although experiments conducted by us showed that AA-0096 had generally good agronomic characteristics when grown under specific conditions, it had significantly lower productivity compared to the generally available commercial brown strains when grown under standard *A. bisporus* conditions, thus making it an unlikely candidate for producing a successful commercial strain.

This difficult genetic background became even more evident when our initial crosses were prepared. A number of test crosses were made between AA-0096 and white or brown commercial *A. bisporus* varieties. None of these test crosses produced hybrids with acceptable agronomic characteristics. All of the crosses between AA-0096 and the commercial whites strains produced cream and tan colored mushrooms too light in color for use as a brown mushroom. The crosses between AA-0096 with the commercial browns produced hybrids with unacceptable commercial productivity or, in some cases, did not even produce mushrooms. It was not until we crossed homokaryons from commercial browns and commercial whites, creating a "bridging cross strain," that we were able to produce darker, more productive mushrooms by introducing the genetic material from AA-0096 via a second cross with the bridging cross strain.

One preferred mushroom strain of the invention contains a mixture of genetic material from the wild AA-0096 strain and the commercial brown strain known as Amycel 2400, as well as genetic material from a commercial white hybrid (a U1 derivative) that was introduced by formation of a bridging cross strain between the commercial strains prior to introduction of genetic material from the wild strain. This particular bridging cross strain, know in our examples as the 4x29 strain, on its own does not produce mushrooms that are dark enough for commercial production as a brown mushroom. Furthermore, the combination of AA-0096 with either the commercial white or commercial brown on their own does not produce commercially acceptable strains. Therefore it was not apparent before the completion of the breeding program that darker cap color and increased productivity could be obtained from using genetic material from the AA-0096 strain.

However, now that the breeding program has been completed, the desirable genetic characteristics of strain AA-0096 can be incorporated into commercial mushroom strains by initially forming a bridging cross strain from any commercial white and any commercial brown *A. bisporus* strains. The bridging cross strain is then crossed further with the AA-0096 strain, and the resulting strains are selected for physical properties as described herein. Commercial strains of white and brown *A. bisporus* mushrooms do not need to be deposited in order for the broader aspects of the invention to be practiced, as they can simply be purchased from suppliers and/or retailers, such as grocery stores, and then crossed to form a bridging cross strain prior to the final cross with strain AA-0096. However, in order to make possible the preparation of all possible crosses of AA-0096 and the specific bridging cross strain (4x29) developed by the present inventors (which constitutes a preferred embodiment of the present invention), strain 4x29 has also been deposited under the provisions of the Budapest Treaty with the American Type Culture Collection, Rockville, Md., USA, ATCC accession No. PTA-6877 (inventors' identification 4x29 *A. bisporus*, deposited on Jul. 20, 2005).

It should be recognized that the mushrooms of the invention are hybrids (equivalent to crosses), as they are formed by the hybridization of wild strain AA-0096 with a second *A. bisporus* strain (with the second strain in some cases being a cross itself between two commercial *A. bisporus* strains, such as the 4x29 strain). Thus the terminology used in recently published U.S. Patent Application No. 20040144020 (which describes a cross between a different wild *A. bisporus* strain and a commercial strain as being a "hybrid mushroom") applies equally well to the present invention, and that application is herein incorporated by reference for all purposes. Such differences in terminology (and in the specific techniques used in that application) are merely indicative of the variety of terminology and techniques used in the mushroom production field.

Genetics of Mushrooms of the Invention

Mushrooms within the scope of the present invention referred to as "clones" can be prepared by any of the known cloning processes (as well as those that may be discovered in the future) from a mushroom of the invention, whether from one of the deposited strains or from a strain that is a progeny of the deposited strains. These clones are prepared without a sexual crossing process and have the same genetic and physical characteristics as their parents. Mushrooms within the scope of the present invention referred to as "progeny," rather than being clones of the deposited mushrooms, are strains that have been obtained by crossing a deposited strain (e.g., AA-0096 or BR06) or one of their progeny with a second mushroom strain and are characterized by having at least one "genetic characteristic" of the strain of the invention that is not present as a corresponding genetic characteristic of the second strain with which it has been crossed. A "genetic characteristic" is any property of the genetic material of a mushroom strain (usually a gene sequence) that is measurable by a standard analytical technique. Examples of genetic characteristics include RAPD, RFLP, AFLP or SCAR bands as they appear on gels using standard analytical techniques. These well-know analytical techniques are described in numerous scientific publications, including the following:

SCAR: Paran, I. and R. W. Michelmore (1993). Development of reliable PCR-based markers linked to downy mildew resistance genes in lettuce. *Theor. Appl. Genet.* 85:985-993.

RAPD: Khush, R. S., Becker, E. & M. Wach (1992). DNA Amplification Polymorphisms of the cultivated mushroom *Agaricus bisporus*. *Appl. Env Microbiol* 59:2971-2977

RFLP: Castle, A. J., P. A. Horgen & J. B Anderson 1987. Restriction fragment length polymorphisms in the mushrooms *Agaricus brunnescnes* and *Agaricus bitorquis*. *Appl Env Microbiol* 53:816-822

AFLP: Mueller UG and Wolfenbarger LL (1999) AFLP genotyping and fingerprinting. *Trends Ecol Evol* 14:389-394.

Such genetic characteristics (and the unique nature of the genetic characteristics of the strains of the invention relative to non-AA-0096-derived strains) are exemplified in the RAPD marker Tables 1 and 2 below. In Table 1, strains that contain a specified genetic fragment are indicated by having a "+" symbol, while strains lacking this fragment are indicated with a "−" symbol. Following this convention, strains that share a genetic characteristic (which can be either the presence or absence of a specific genetic fragments) will have corresponding "+" or "−" symbols (i.e., +/+ or −/−). A number of different gene characteristics (which show as a + for one strain and a − for the other) can be observed in the strains of the invention relative to the Amycel 2400 strain (a commercial brown strain that is one of the parents crossed to make the bridging cross strain). Similar unique differences can be seen relative to the parent bridging cross strain 4x29 that contains genetic material from both a brown and a white commercial strain. The fragments different from those of the parent 2400 or 4x29 strains were inherited from the AA-0096 parent and are unique to its progeny. For example, a 910 bp fragment is present in AA-0096 and BR06 strains that is not present in either 4x29 or Amycel 2400. This band is just one of many characteristics bands that can be used to identify strains of the invention.

TABLE 1

|  | 4 × 29 | 2400 | AA-0096 | BR06 |
|---|---|---|---|---|
| OP-C4$_{1400}$ | + | + | − | − |
| OPC-4$_{910}$ | − | − | + | + |
| OPC-7$_{1200}$ | − | − | + | + |
| OPC-8$_{500}$ | − | − | + | + |
| OPC-8$_{450}$ | − | − | + | + |
| OPC-10$_{420}$ | − | − | + | + |
| OPC-11$_{700}$ | − | − | + | + |
| OPC-11$_{600}$ | − | − | + | + |
| OPC-13$_{1300}$ | − | − | + | + |
| OPF-5$_{1900}$ | − | − | + | + |
| OPF-8$_{200}$ | + | + | − | − |
| OPF-9$_{2200}$ | − | − | + | + |
| OPF-11$_{1100}$ | − | − | + | + |
| OPH-1$_{2500}$ | + | + | − | − |
| OPH-1$_{1700}$ | − | − | + | + |
| OPH-5$_{1900}$ | − | − | + | + |
| OPH-6$_{1200}$ | − | − | + | + |
| OPH-16$_{480}$ | − | − | + | + |
| OPH-18$_{1400}$ | − | − | + | + |
| OPH-18$_{1000}$ | + | + | − | − |
| OPL-6$_{1800}$ | + | + | − | − |
| OPL-6$_{2100}$ | + | + | − | − |
| OPL-8$_{1200}$ | − | − | + | + |

TABLE 1-continued

|  | 4 × 29 | 2400 | AA-0096 | BR06 |
|---|---|---|---|---|
| OPJ-4$_{1500}$ | − | − | + | + |
| OPJ-5$_{1800}$ | − | − | + | + |
| OPJ-5$_{1200}$ | + | + | − | − |
| OPJ-7$_{1850}$ | − | − | + | + |
| OPK-1$_{690}$ | − | − | + | + |
| OPK-1$_{810}$ | + | + | − | − |
| OPK-8$_{900}$ | − | − | + | + |

TABLE 2

|  | Sequences |
|---|---|
| OPC-4 | CCGCATCTAC (SEQ ID NO: 0001) |
| OPC-7 | GTCCCGACGA (SEQ ID NO: 0002) |
| OPC8 | TGGACCGGTG (SEQ ID NO: 0003) |
| OPC-10 | TGTCTGGGTG (SEQ ID NO: 0004) |
| OPC-11 | AAAGCTGCGG (SEQ ID NO: 0005) |
| OPC-13 | AAGCCTCGTC (SEQ ID NO: 0006) |
| OPF-5 | CCGAATTCCC (SEQ ID NO: 0007) |
| OPF-8 | GGGATATCGG (SEQ ID NO: 0008) |
| OPF-9 | CCAAGCTTCC (SEQ ID NO: 0009) |
| OPF-11 | TTGGTACCCC (SEQ ID NO: 0010) |
| OPH-1 | GGTCGGAGAA (SEQ ID NO: 0011) |
| OPH-5 | AGTCGTCCCC (SEQ ID NO: 0012) |
| OPH-6 | ACGCATCGCA (SEQ ID NO: 0013) |
| OPH-16 | TCTCAGCTGG (SEQ ID NO: 0014) |
| OPH-18 | GAATCGGCCA (SEQ ID NO: 0015) |
| OPJ-4 | CCGAACACGG (SEQ ID NO: 0016) |
| OPJ-5 | CTCCATGGGG (SEQ ID NO: 0017) |
| OPJ-7 | CCTCTCGACA (SEQ ID NO: 0018) |
| OPJ-9 | TGAGCCTCAC (SEQ ID NO: 0019) |
| OPK-1 | CATTCGAGCC (SEQ ID NO: 0020) |

TABLE 2-continued

Sequences

| | |
|---|---|
| OPK-6 | CACCTTTCCC (SEQ ID NO: 0021) |
| OPK-8 | GAACACTGGG (SEQ ID NO: 0022) |
| OPL-8 | AGCAGGTGGA (SEQ ID NO: 0023) |

Similar unique genetic characteristics can be seen in SCAR data set out in Tables 3-6. For example, Tables 3 and 4 show that a 550 bp fragment is found in the BR06 strain, one of the progeny of AA-0096, as well as in AA-0096 itself, using the primer sequences for R&D#9 described in Table 5, but is not found in Amycel 2400 or Sylvan 600 (commercial brown strains). Accordingly, this sequence can be used in the process of identifying progeny of AA-0096. In a similar manner, any of the R&D series makers unique for AA-0096 identified in the tables herein can be used to identify the progeny of AA-0096 crossed with 4x29 and differentiate them from Amycel 2400, other commercial brown strains, or future brown mushroom strains created using breeding programs that do not involve AA-0096. In a similar manner, unique gene fragments can be found that distinguish the progeny from a white mushroom strain (a U1 derivative in our example), other commercial white strains, or future white mushroom strains created using breeding programs that do not involve AA-0096.

TABLE 3

Variations from commercial brown strain Amycel 2400

| Marker | Amycel 2400 | BR06 | AA-0096 |
|---|---|---|---|
| R&D#17 | 480/450/396 | 460/450/396 | 460/450/396 |
| R&D#9 | 520 | 550/520/510 | 550/520/510 |
| R&D#70[1] | 480/120 | 500/290/120 | 500/290/120 |
| R&D#55[2] | 490/300/200/60 | 490/450/300/200/60 | 490/450/300/200/60 |

[1]To obtain results product was cut with Restriction Enzyme Hinf I
[2]To obtain results product was cut with Restriction Enzyme Taq I

TABLE 4

Variations from commercial brown strain Sylvan 600

| Marker | Sylvan 600 | BR06 |
|---|---|---|
| R&D#17 | 480/450/396 | 460/450/396 |
| R&D#9 | 510 | 550/520/510 |
| R&D#70[1] | 520/510 | 500/290/120 |
| R&D#55[2] | 200 | 490/450/300/200/60 |

[1]To obtain results product was cut with Restriction Enzyme Cfo1
[2]To obtain results product was cut with Restriction Enzyme Rsa1

TABLE 5

Sequence of primer fragments

| | R&D #17 | R&D #9 | R&D #70 | R&D #55 |
|---|---|---|---|---|
| Forward primer 5' | aggtgcgatgtcgtccctca (SEQ ID NO: 0024) | gtcccggtgtgacca (SEQ ID NO: 0026) | ccttccaagaaaacccact (SEQ ID NO: 0028) | tggtcacagaaggtcctcag (SEQ ID NO: 0030) |
| Reverse prime 5' | tgggtgggatacttcgctgg (SEQ ID NO: 0025) | gccatgagcgatcat (SEQ ID NO: 0027) | atttccgagatcaccgaga (SEQ ID NO: 0029) | cgcatacattccaagagcac (SEQ ID NO: 0031) |

TABLE 6

Variations from other commercial brown strains

| Marker | Sylvan SB65 | Sylvan 600 | Lambert 800 | Lambert 801 | Amycel 2400 | BR06 | AA-0096 |
|---|---|---|---|---|---|---|---|
| R&D#17 | 480/450/396 | 480/450/396 | 480/450/396 | 480/450/396 | 480/450/396 | 460/450/396 | 460/450/396 |
| R&D#9 | 520 | 520 | 520 | 520 | 520 | 550/520/510 | 550/520/510 |
| R&D#70[1] | 480/120 | 480/120 | 480/120 | 480/120 | 480/120 | 500/290/120 | 500/290/120 |
| R&D#55[2] | 490/300/200/60 | 490/300/200/60 | 490/300/200/60 | 490/300/200/60 | 490/300/200/60 | 490/450/300/200/60 | 490/450/300/200/60 |

[1]To obtain results product was cut with Restriction Enzyme Cfo1
[2]To obtain results product was cut with Restriction Enzyme Rsa1

Characteristic genetic information identified as shown herein (or by any other technique) for other mushroom strains or species used in a crossing program can be used to help identify progeny of the deposited strains. Generally, the more characteristic bands that are present, the more closely the progeny will resemble the parent. The first-generation class of progeny strains derived from AA-0096 theoretically will share numerous genetic characteristics with AA-0096, which will be apparent by both SCAR analysis and RAPD analysis. Although no further crosses are required to obtain mushrooms of the invention, additional crosses may be carried out to add other genetic characteristics or in attempts to disguise the lineage of the strain. After several crosses, only a few characteristic bands may be present (depending on random reassortinent process during meiosis). Preferred strains retain at least 5, preferably at least 10, unique RAPD bands from AA-0096 or at least 2, preferably at least 5, characteristic RFLP or SCAR bands.

Although the current examples describe comparison of strains of the invention with the commercial brown strain that is one of their ancestors via the crossing program described herein, comparisons can be made to any strain to show the differences of AA-0096 progeny from that strain.

In addition to characteristic bands associated with the genetic material derived from AA-0096, a mushroom strain obtained by crossing a strain of the invention with a different mushroom strain will have genetic characteristics of the second strain; e.g., the mushroom strain, in addition to having a characteristic RAPD or RPLP band derived from AA-0096 will have at least one RAPD or RFLP band in common with the second strain (e.g., Amycel 2400) that is not present as a corresponding RAPD or RFLP band from strain AA-0096. These characteristic bands will be useful in identifying the second strain that has been crossed with a parent strain of the invention to give a progeny strain of the invention.

Selection of Desired Progeny

Any progeny strain genetically derived from AA-0096 that retains a commercially desirable characteristic of the strains of the invention remains within the scope of the invention. Such brown progeny strains (relative to the standard) can readily be selected by color analysis of mushroom caps, mushroom cap thickness measurement, antagonism with the commercial brown strain 2400, and significantly different productivity after crossing, as well as the identification of genetic characteristics. The commercially desirable characteristics can be measured quantitatively using the following general techniques, which are illustrated by specific techniques in the Examples that follow:

Productivity: fruit strains in a controlled environment and collect weight data on all mushrooms produced.

Cap color: measure color of caps using a color analysis instrument.

Cap thickness: measure cap width and divide by cap height to obtain a ratio.

Genetic antagonism: attempt to cross strain under consideration with commercial brown and white existing strains; genetically antagonistic strains will not produce viable crosses.

Some or all of these characteristics may be present in progeny of the invention, depending on genetic sorting. All progeny will have genetic bands in common with AA-0096 and one or more of these physical characteristics.

Cap Color

Whiteness, or brightness, is measured by ability to reflect all wavelengths of visible light. Following this definition, mushroom strains that reflected less light would be considered darker or less white. The Specific measurement techniques are set forth in detail in the Examples, but other measurement techniques can be used as well, as long as the same technique is used to measure whiteness (darkness) of both the strains of the invention and the reference Amycel 2400 strain. A given strain will be sufficiently darker to be considered within the scope of the invention when the strain has a white light reflectance significantly less than that of strain 2400 at a confidence level of at least 95% when measured by a single reflectance measurement technique. Statistical analysis is by standard techniques such as those described in N. M. Downie and R. W. Heath, Basic Statistical Methods, Harper & Brothers, New York, 1959 (see especially chapter 12, pp. 123-139, entitled "Testing Difference Between Means"). Strain 2400 has a typical mean reflectance of 60%. Strains of the invention typically have a reflectance less than 58% (significant difference at 95% confidence level), preferably less than 56%, more preferably less than 54%.

Increased Productivity

Mushroom productivity is measured by comparing total crop yield means expressed in pounds of mushrooms produced per square foot of growing area. Data is gathered over the three standard "breaks" of the growing cycle. The specifics of mushroom growing are set forth in the Examples. Strains of the invention typically will yield the same as 2400 (no significant difference at 95% confidence level), preferably have yield that is 5% higher then 2400 (significant difference at 95% confidence level), more preferably a yield that is 10% greater then 2400 (significant difference at 95% confidence level).

Thicker Cap/Cap Shape (CS)

The invented class produces brown mushrooms with thicker more domed shape caps, giving them a distinct shape compared to Amycel 2400. Cap measurements can be compared between randomly selected mushrooms of the invention and a commercially available brown mushroom, such as Amycel 2400. Measurement data is typically collected from 20-50 harvested mushrooms grown and picked under specific and standard growing conditions. Cap shape (CS) can be quantified by first measuring the height of the cap (HC), the distance from the top of the cap adjacent to the mushroom stem to the top of the gills, and dividing this result by cap diameter (CD).

Non-Compatibility

The mycelia of compatible strains of mushrooms are able to fuse together (anastomose) and share nuclear constituents. Anastomosis also facilitates the transportation of nutrients between the two strains. Non-compatible strains can be defined as strains where this type of mycelial fusion is not possible or is reduced; in other words, anastomosis cannot occur or is hindered. An experiment can be carried out to quantify this phenomenon. Standard mushroom growing utilizes two inoculated substrates, inoculated or spawned compost and inoculated casing or "cac". Normally both of these substrates contain the same mushroom strain, which when combined and incubated under standard growing conditions produce commercially acceptable yields of mushrooms. Mycelium of the invented class, including BR06, that are not compatible with Amycel 2400 or other commercial brown mushrooms strains, will give different results. Combination of these two strains in the compost and the casing will result in retarded growth and lower mushroom yields, demonstrating non-compatibility. The lack of anastomosis between strains has the potential of limiting the infection and spread of viral disease (Kerrigan, R., Mushroom News Volume 53 Number 14-23 (2005)).

In contrast to the first three commercially desirable characteristics, in which the improved properties can be said to be "better" than the corresponding properties of the references strain (better being darker, more productive, and thicker, respectively), non-compatibility is more of an absolute: two strains are either compatible or not, although there can be different degrees of compatibility as indicated by the co-growth assay described in the preceding paragraph. Accordingly, while the present invention achieves better commercial properties of cap color, productivity, and cap thickness relative to the standard, non-compatibility is best described as simply being present, rather than being "better." However, the disease resistance will be better in many cases when the disease attacks a mushroom characteristic based on the genetics of the currently available (and substantially genetically identical) brown *Agaricus bisporus* commercial strains.

Inheritance of Markers

The RAPD and SCAR data shown in the tables above clearly show the segregation of markers into BR06. We concentrated on identifying loci inherited from AA-0096, as these loci are absent from Amycel 2400 brown mushrooms. However, the markers shown in the examples are not the only markers that can be used to characterize the strains and progeny strains of the invention, and the invention should not be considered limited to the example markers.

Novelty of the New Hybrid Strains

The uniqueness of the new hybrids is shown by the SCAR and RAPD results. BR06 is the product of a unique nuclear fusion event (or cross) and has inherited markers from both AA-0096 and 4x29. This invention, due to its novel genetics, may offer improved resistance to known and emerging mushroom pathogens (the importance of novel genetic characteristics in providing disease resistance is discussed in Kerrigan, R., Mushroom News Volume 53 Number 14-23 (2005)). BR06 is a particularly preferred embodiment of the invention and, in addition to be a representative of the general class of AA-0096 progeny with improved characteristics, is also a representative of the preferred class of crosses between the 4x29 bridging cross strain and the wild AA-0096 parent. All crosses between the 4x29 bridging cross strain and the wild AA-0096 parent that have at least one improved characteristic noted herein (preferably at least two, more preferably at least 3, and most preferably all four) are members of this preferred class of crosses.

Production of Commercial Mushrooms from the New Hybrid Strains

As the hybrid mushrooms of the invention remain *Agaricus bisporus* mushroom strains, they can be grown using standard commercial mushroom growing processes that have been developed for *Agaricus bisporus*. Such processes are well known in the industry and need not be described here in detail. Examples of techniques for mushroom production are shown in numerous patents and technical publications, including those cited herein, with details of production also being shown in the Examples that follow. In general, the process comprises inoculating a mushroom growth medium with a hybrid *Agaricus bisporus* mushroom strain of the invention, maintaining the inoculated growth medium under conditions conducive to mushroom fruiting, and collecting mushrooms from the growth medium after they have reached the desired maturity level (e.g., for crimini or portabellas).

The invention now being generally described, specific examples are provided showing various embodiments of the invention. The invention, however, is not limited to these specific embodiments.

EXAMPLES

Strains

As noted previously, strains 4x29 and AA-0096 can now be obtained from ATCC, along with preferred strain BR06, which was deposited under the provisions of the Budapest Treaty with the American Type Culture Collection, Rockville, Md., USA, ATCC accession No. PTA-6876 (inventors' identification BR06 *A. bisporus*, deposited on Jul. 20, 2005). Mycelium of mushroom strain AA-0096 was used from our own collection; when others reproduce the present invention, this strain can be obtained through the ATCC. Mycelium from commercial strain Amycel 2400 (material provided by Amycel, San Juan Bautista, Calif. 94045) and commercial strain 901 (Lambert Spawn Company, PA) was used in creating breeding lines, including the bridging cross strains previously described. Among the examples of the breeding lines produced by this initial bridging cross is the 4x29 strain used in making certain preferred embodiments of the invention.

All strains were cultured, maintained, and selected on Compost Lite Agar (CL) at 21 .degree. C. CL Agar comprises potato dextrose agar (PDA; Difco) with 0.5% Yeast extract (Sigma) and 10% compost extract. Compost extract was made by infusing equal volumes (w/v) of phase II compost and $H_2O$. The compost and water were autoclaved twice for 90 minutes, and the aqueous extract was added to make CL agar. Mushroom spawn was made using rye grain inoculated with 2 $cm^2$ chunks of colonized CL agar. Spawn was grown for four weeks and was shaken at bi-weekly intervals.

Compost and Media

Heterokaryons were fruited on standard phase II mushroom compost. The compost was colonized with inoculated rye spawn for thirteen to fourteen days, with bed temperatures in the range 21°-27° C., and $CO_2$ between 5000 and 10000 parts per million (ppm). Beds were then covered with a 5-cm layer of casing formulation (approximately 75% peat/25% $CaCO_3$), and the cased beds were scratched after five days to encourage mycelial growth into the casing layer. Two days after scratching the beds were flushed, with the air temperature dropping to 16° C. and the $CO_2$ dropping to 1000 to 1500 ppm. Mushrooms appeared approximately two weeks after flushing, and during first break bed temperatures were held at 18°-21° C. For every crop, yield was assessed using three breaks of production.

DNA Isolation for PCR Analysis

For DNA isolation, cultures were either grown in MPYFE liquid medium (Castle et al., 1987) or on cellophane over CL Agar. Harvested tissue was frozen at −70° C. and was freeze dried prior to DNA isolation.

DNA was prepared from freeze-dried mycelium. First, freeze dried tissue was ground with a glass rod, and 0.6 ml of 65° C. DNA extraction buffer (0.7 M sodium chloride/0.1 M sodium sulphite/0.1 M Tris-HCl, pH 7.5/0.05 M EDTA/1% SDS) was added. Tubes were mixed and placed at 65° C. for 30 minutes. Next, 0.6 ml of chloroform:isoamyl alcohol (24:1) was added, and the tubes were mixed. Tubes were placed on ice for 30 minutes, followed by centrifugation at high speed (12000×g) for 30 minutes.

Supernatants were placed in fresh tubes, and 2 volumes of ethanol were added. After mixing, the tubes were centrifuged at low speed (2000×g) for 30 seconds. Pellets were resuspended in 200 µl sterile water, and 100 µl of 7.5 M ammonium acetate were added. The tubes were then mixed and placed on ice for 1 hour.

Next, the tubes were spun at high speed (12000×g) for 30 minutes, and the supernatants were transferred to fresh tubes. Isopropanol (0.54 volume) was added, and the tubes were mixed by gentle inversion. Supernatants were removed, and pellets were washed with 70% ethanol. Finally, ethanol was removed through centrifugation and pipetting, and the DNA was resuspended in 100 µl of TE (10 mM Tris-HCl, pH 7.5/1 mM EDTA).

Derivation and Isolation of Homokaryons

All homokaryons used in the invention were derived from spontaneous homokaryons identified from single spore isolates (SSI). Spores were collected from mushrooms, and the spores were diluted in $H_2O$ containing 1% Tween 80. Spore density was calculated on a haemocytometer slide, and spore dilutions were plated out on PDA.

DNA Fingerprinting

For both parents (4x29 and AA-0096), SCAR makers derived from RAPD markers (Paran, I. and R. W. Michelmore (1993); Development of reliable PCR-based markers linked to downy mildew resistance genes in lettuce; *Theor. Appl. Genet* 85:985-993) were used to determine the homokaryotic nature of the single spore isolates.

Compatibility of homokaryons of both strains was determined by using techniques described using the MAT marker (Xu J, Kerrigan R W, Horgen P A, Anderson J B (1993). Localization of the mating type gene in *Agaricus bisporus*. Appl Environm. Microbiol 59:3044-3049), and by doing test crosses.

Homokaryons derived from 4x29 were screened for color using the L43 SCAR described by Loftus, M., L. Bouchti King and C. Robles (2000) Science and Cultivation of Edible Fungi: 201-202.

DNA fingerprinting of novel strains was determined by polymerase chain reaction (PCR) analysis using sequence-characterized amplified region markers (SCAR) markers and RAPD markers. DNA fingerprinting techniques were adapted from those described in Khush, R. S., Becker, E. & M. Wach (1992); DNA Amplification Polymorphisms of the cultivated mushroom *Agaricus bisporus; Appl. Env Microbiol* 59:2971-2977, and Williams, J.A., Kubeliki, K., Livat, K., Rafalski, J. & S. Tingey. (1991); DNA polymorphisms amplified by arbitrary primers are useful as genetic markers; Nuclei Acids Research. 22:6531-6525.

Hybrid Mushrooms Derived from Strain AA-0096 (syn. BP1)

Initial experiments were carried out to determine if wild strains of *A. bisporus* could be used to improve commercial strains, specifically to improve upon the commercial brown *A. bisporus* strain used to produce portabella (syn. portabello) and cremini (small unopened brown mushrooms) varieties. Various genetically identical versions of this brown strain are sold by U.S. mushroom spawn producers. The strain designated Amycel 2400 was used as the primary representative of this class for comparative purposes.

The hybrid known as 4x29 (now available as ATCC accession No. PTA-6877) was chosen as the variety to be crossed with AA-0096 because of its ability to produce mushrooms with increased cap thickness when compared to Amycel 2400, a potential benefit to crop yield. The hybrid 4x29 was created by combining compatible homokaryotic single spore isolates of the Amycel 2400 with homokaryotic single spore isolate of a commercially available off-white hybrid (present day version of the Horst U1 hybrid).

A total of 105 homokaryotic single spore isolates were collected from AA-0096. The nuclear constitution of the isolates was analyzed using SCAR markers.

A total of 250 homokaryotic single spores isolates were collected from 4x29. The nuclear constitution of the isolates was analyzed using SCAR makers. Due to the nature of this hybrid additional analysis to determine the color loci inherited by each homokaryon was also undertaken using SCAR markers.

Compatible homokaryons of AA-0096 and 4x29 were crossed and the resulting progeny were screened for darker cap color and increased yield. A number of the progeny, including a new hybrid designated BR06 (ATCC accession No. PTA-6876), exhibited darker caps and increased yield when compared to the commercial brown strain (Amycel 2400).

Yield Data

A series of three crops were grown to compare BR06 to the commercial brown strain Amycel 2400. The crops were undertaken at the Amycel Intermediate Testing Facility. Both strains were fruited in small 1.8 ft² mushroom trays on standard phase II mushroom compost. The compost was colonized with inoculated rye-grain spawn for fifteen days, with bed temperatures in the range 21°-27° C., and $CO_2$ between 5000 and 10000 parts per million (ppm). Beds were then covered with a 5-cm layer of casing formulation (approximately 75% peat/25% $CaCO_3$), and the cased beds were scratched after five days to encourage mycelial growth into the casing layer. Three days after scratching the beds were flushed, with the air temperature dropping to 16° C. and the $CO_2$ dropping to 1000 to 1500 ppm. Mushrooms appeared approximately two weeks after flushing. Mushrooms were harvested over a three-week period, and comprehensive yield data was collected using a system designed specifically for this purpose. The mean yield of the two strains expressed in pounds of mushrooms produced per square foot data for the three trials is summarized below in Table 7.

TABLE 7

|  | BR06 | Amycel 2400 |
| --- | --- | --- |
| Trial#1 | 6.41$^a$ | 5.49$^b$ |
| Trial#2 | 6.39$^a$ | 5.28$^b$ |
| Trial#3 | 6.64$^a$ | 5.65$^b$ |

Any two means having a common letter are not significantly different at the 5% level of significance, using standard t-test analysis.

As can be seen from the data, the BR06 significantly out yielded the Amycel 2400 strain in every case.

Color Measurements

Mushroom surface color data was evaluated with a chromameter (Konica Minolta BC-10, Osaka, Japan), by measuring the L* and b* parameters. L* is a brightness variable and extends from 0 (black) to 100 (white). The b* value represents yellowness-blueness chromaticity.

Mushrooms of cap diameter 8-10 cm were collected from both BR06 and Amycel 2400 at the same crop stage, and measurements were taken on the tops of the caps at random. Thirty L* and b* values for each strain was analyzed using standard t-test analysis (Microsoft EXCEL 2000 Data Analysis Package). Data is analyzed in Table 8.

TABLE 8

|  | Amycel 2400 | BR06 |
| --- | --- | --- |
| L* Value | 60.15$^a$ | 56.66$^b$ |
| b* Value | 11.6$^a$ | 13.64$^b$ |

Any two means having a common letter are not significantly different at the 5% level of significance, using standard t-test analysis.

BR06 produced mushrooms that were both less bright (Lower L* value) and more yellow (higher b* Value) then the commercial brown Amycel 2400.

Cap Shape

Four experiments were undertaken to compare the Cap Shape (CS) of BR06 versus Amycel 2400. Cap Shape is the ratio of cap height (CH) and cap diameter (CD). In all experiments, 40 mushrooms were randomly selected from each treatment from small experimental trays, grown according to standard mushroom growing conditions (conditions summarized above under Yield Data). In all of the experiments mushrooms were harvested at the same time.

The data from all of the above experiments are summarized in Table 9. Statistical analysis of the Cap Shape ratio was completed utilizing Microsoft Excel 2000. As can be seen in all trials, the BR06 strain produced mushrooms with a higher Cap Shape value than the Amycel 2400. Cap Shape differences ranged from 0.02 to 0.05. The mushrooms produced by BR06 were noticeably thicker upon observation, and this carried out into the values obtained through measurement.

|  | BR06 | Amycel 2400 |
|---|---|---|
| Experiment#1 | $0.29^a$ | $0.27^b$ |
| Experiment#2 | $0.26^a$ | $0.22^b$ |
| Experiment#3 | $0.32^a$ | $0.30^b$ |
| Experiment#4 | $0.30^a$ | $0.25^b$ |

Any two means having a common letter are not significantly different at the 5% level of Significance, using standard t-test analysis.

Non-Compatibility

Two experiments were completed to demonstrate the non-compatibility between BR06 and Amycel 2400. Treatment#1 and Treatment#3 are the un-mixed treatments (same strain in compost and casing) and Treatment#2 and Treatment#4 are the mixed treatments (different strain in compost and casing). Five trays of each of all of the treatments were grown in small growing rooms, according to standard mushroom growing practices (conditions summarized above under Yield Data).

At the time of scratch and flush, the growth of mushroom mycelium in the casing layer of the trays of the mixed treatments (#2 and #4) was greatly diminished compared to growth in the non-mixed treatments (#1 and #3). During mushroom fruiting the number of mushroom pins produced by the mixed treatments was greatly reduced in both of the mixed treatments (BR06/Amycel 2400 and Amycel 2400/BR06) versus the non-mixed treatments.

As can be seen in the tables, the total yield for the mixed treatments was greatly reduced versus the non-mixed treatments (yield is expressed as pounds of mushrooms per square foot of growing area).

TABLE 10

|  | Treatment#1 | Treatment#2 |
|---|---|---|
| Strain Compost | BR06 | BR06 |
| Strain Casing | BR06 | Amycel 2400 |
| Experiment#1 | $6.52^a$ | $3.63^b$ |
| Experiment#2 | $4.91^a$ | $1.87^b$ |

Any two means having a common letter are not significantly different at the 5% level of Significance, using standard t-test analysis.

TABLE 11

|  | Treatment#3 | Treatment#4 |
|---|---|---|
| Strain Compost | Amycel 2400 | Amycel 2400 |
| Strain Casing | Amycel 2400 | BR06 |
| Experiment#1 | $6.04^a$ | $1.56^b$ |
| Experiment#2 | $4.97^a$ | $2.23^b$ |

Any two means having a common letter are not significantly different at the 5% level of Significance, using standard t-test analysis.

The reduction in yield when BR06 and Amycel 2400 are mixed together indicates a reduction of anastomosis between the two strains.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A hybrid *Agaricus bisporus* mushroom strain, wherein the hybrid strain is a cross of a mushroom of wild strain AA-0096 with an *Agaricus bisporus* bridging cross strain, wherein the bridging cross strain is a cross of a commercial white *Agaricus bisporus* strain and a commercial brown *Agaricus bisporus* strain not derived from wild strain AA-0096, wherein a representative culture of said wild strain AA-0096 is available from ATCC under Accession No. PTA-6903 and wherein said hybrid has at least one physical characteristic selected from the group consisting of a darker cap color, a thicker cap, and a higher productivity as compared to the corresponding physical characteristics of comparison strain Amycel 2400.

2. The hybrid strain of claim 1, wherein said hybrid strain is a progeny of AA-0096 and has at least one RAPD, SCAR or RFLP band in common with strain AA-0096 that is not present as a corresponding RAPD, SCAR or RFLP band from commercial brown *Agaricus bisporus* strain Amycel 2400, or at least one RAPD, SCAR or RFLP band in common with *Agaricus bisporus* bridging cross strain 4x29 that is not present as a corresponding RAPD, SCAR or RFLP band from strain AA-0096, and wherein a representative culture of said bridging cross strain 4x29 is available from ATCC under Accession No. PTA-6877.

3. The hybrid strain of claim 2, wherein said hybrid strain further comprises at least five RAPD or two RFLP or SCAR bands in common with strain AA-0096 that are not present as corresponding RAPD, RFLP or SCAR bands from commercial brown *Agaricus bisporus* strain Amycel 2400.

4. The hybrid strain of claim 1, wherein said hybrid strain comprises at least one RAPD+ marker present in strain BR06 as shown in Table 1, and wherein a representative culture of said strain BR06 is available from ATCC under Accession No. PTA-6876.

5. The hybrid strain of claim 1, wherein said hybrid strain has all genetic characteristics of strain BR06, and wherein a representative culture of said strain BR06 is available from ATCC under Accession No. PTA-6876.

6. A hybrid mushroom culture of *Agaricus bisporus*, wherein the hybrid mushroom culture is a cross of a first culture of *Agaricus bisporus* with a second culture of *Agaricus bisporus*, wherein said first culture of *Agaricus bisporus* is a wild strain designated AA-0096, a representative culture of said wild strain AA-0096 available from ATCC under Accession No. PTA-6903, wherein said second culture of *Agaricus bisporus* is a culture of an *Agaricus bisporus* bridging cross strain, and wherein the bridging cross strain is a cross of a commercial white *Agaricus bisporus* strain and a commercial brown *Agaricus bisporus* strain not derived from wild strain AA-0096, wherein said culture produces a mushroom having at least one physical characteristic selected from the group consisting of a darker cap color, a thicker cap, and a higher productivity as compared to the corresponding physical characteristics of comparison strain Amycel 2400.

7. The hybrid mushroom culture of claim 6, wherein said commercial white *Agaricus bisporus* strain is U1, U3, a U1 derivative, or a Horst U1/U3 hybrid.

8. The hybrid mushroom culture of claim 6, wherein said hybrid mushroom culture produces mushrooms having a brown color darker than commercial brown *Agaricus bisporus* strain Amycel 2400.

9. The hybrid mushroom culture of claim 6, wherein said hybrid mushroom culture exhibits antagonism toward strains in a Horst U1/U3 lineage group or to commercial brown *Agaricus bisporus* strain Amycel 2400.

10. Inoculum comprising the hybrid mushroom culture of claim 6.

11. Mushroom spawn comprising the inoculum of claim 10.

12. Casing inoculant comprising the inoculum of claim 10.

13. Homokaryons derived from the hybrid mushroom culture of claim 6.

14. Mushrooms produced by fruiting of the hybrid mushroom culture of claim 6.

15. A method of producing commercial brown mushrooms, which comprises: inoculating a mushroom growth medium with the hybrid *Agaricus bisporus* mushroom strain of claim 1; maintaining said inoculated growth medium under conditions conducive to mushroom fruiting; and collecting mushrooms from said growth medium.

16. The hybrid strain of claim 1, wherein said commercial white *Agaricus bisporus* strain is U1, U3, a U1 derivative, or a Horst U1/U3 hybrid and said commercial brown *Agaricus bisporus* strain is Amycel 2400.

17. The hybrid strain of claim 1, wherein said bridging cross strain is a 4x29 strain available from ATCC under Accession No. PTA-6877.

18. The hybrid strain of claim 1, wherein said hybrid strain has a mean reflectance of less than 60%.

19. The hybrid strain of claim 1, wherein said hybrid strain has a total crop yield that is equal to or higher than the total crop yield of commercial brown *Agaricus bisporus* strain Amycel 2400 when grown under similar conditions.

20. The hybrid strain of claim 1, wherein said hybrid strain has a cap shape that is higher than the cap shape of commercial brown *Agaricus bisporus* strain Amycel 2400 when grown under similar conditions and harvested at the same time.

21. The hybrid strain of claim 1, wherein said hybrid strain is genetically non-compatible with commercial brown *Agaricus bisporus* strain Amycel 2400.

22. The hybrid mushroom culture of claim 6, wherein said bridging cross strain is a 4x29 strain available from ATCC under Accession No. PTA-6877.

23. An *Agaricus bisporus* BR06 mushroom strain or a homokaryon derived thereof, wherein a representative culture of said BR06 is available from ATCC under Accession No. PTA-6876.

* * * * *

UNITED STATES PATENT AND TRADEMARK OFFICE
CERTIFICATE OF CORRECTION

PATENT NO. : 7,608,760 B2  
APPLICATION NO. : 11/267043  
DATED : October 27, 2009  
INVENTOR(S) : Robles et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 815 days.

Signed and Sealed this

Twelfth Day of October, 2010

David J. Kappos  
*Director of the United States Patent and Trademark Office*

SEQUENCE LISTING

<160> NUMBER OF SEQ ID NOS: 31

<210> SEQ ID NO 1
<211> LENGTH: 10
<212> TYPE: DNA
<213> ORGANISM: Artificial
<220> FEATURE:
<223> OTHER INFORMATION: Primer

<400> SEQUENCE: 1
ccgcatctac            10

<210> SEQ ID NO 2
<211> LENGTH: 10
<212> TYPE: DNA
<213> ORGANISM: Artificial
<220> FEATURE:
<223> OTHER INFORMATION: Primer

<400> SEQUENCE: 2
gtcccgacga            10

<210> SEQ ID NO 3
<211> LENGTH: 10
<212> TYPE: DNA
<213> ORGANISM: Artificial
<220> FEATURE:
<223> OTHER INFORMATION: Primer

<400> SEQUENCE: 3
tggaccggtg                                                              10

<210> SEQ ID NO 4
<211> LENGTH: 10
<212> TYPE: DNA
<213> ORGANISM: Artificial
<220> FEATURE:
<223> OTHER INFORMATION: Primer

<400> SEQUENCE: 4
tgtctgggtg                                                              10

<210> SEQ ID NO 5
<211> LENGTH: 10
<212> TYPE: DNA
<213> ORGANISM: Artificial
<220> FEATURE:
<223> OTHER INFORMATION: Primer

<400> SEQUENCE: 5
aaagctgcgg                                                              10

<210> SEQ ID NO 6
<211> LENGTH: 10
<212> TYPE: DNA
<213> ORGANISM: Artificial
<220> FEATURE:
<223> OTHER INFORMATION: Primer

<400> SEQUENCE: 6
aagcctcgtc                                                              10

<210> SEQ ID NO 7
<211> LENGTH: 10
<212> TYPE: DNA
<213> ORGANISM: Artificial
<220> FEATURE:
<223> OTHER INFORMATION: Primer

<400> SEQUENCE: 7
ccgaattccc                                                              10

<210> SEQ ID NO 8
<211> LENGTH: 10
<212> TYPE: DNA
<213> ORGANISM: Artificial
<220> FEATURE:
<223> OTHER INFORMATION: Primer

<400> SEQUENCE: 8
gggatatcgg                                                              10

<210> SEQ ID NO 9
<211> LENGTH: 10
<212> TYPE: DNA
<213> ORGANISM: Artificial
<220> FEATURE:

-continued

```
<223> OTHER INFORMATION: Primer

<400> SEQUENCE: 9
ccaagcttcc                                                              10

<210> SEQ ID NO 10
<211> LENGTH: 10
<212> TYPE: DNA
<213> ORGANISM: Artificial
<220> FEATURE:
<223> OTHER INFORMATION: Primer

<400> SEQUENCE: 10
ttggtacccc                                                              10

<210> SEQ ID NO 11
<211> LENGTH: 10
<212> TYPE: DNA
<213> ORGANISM: Artificial
<220> FEATURE:
<223> OTHER INFORMATION: Primer

<400> SEQUENCE: 11
ggtcggagaa                                                              10

<210> SEQ ID NO 12
<211> LENGTH: 10
<212> TYPE: DNA
<213> ORGANISM: Artificial
<220> FEATURE:
<223> OTHER INFORMATION: Primer

<400> SEQUENCE: 12
agtcgtcccc                                                              10

<210> SEQ ID NO 13
<211> LENGTH: 10
<212> TYPE: DNA
<213> ORGANISM: Artificial
<220> FEATURE:
<223> OTHER INFORMATION: Primer

<400> SEQUENCE: 13
acgcatcgca                                                              10

<210> SEQ ID NO 14
<211> LENGTH: 10
<212> TYPE: DNA
<213> ORGANISM: Artificial
<220> FEATURE:
<223> OTHER INFORMATION: Primer

<400> SEQUENCE: 14
tctcagctgg                                                              10

<210> SEQ ID NO 15
<211> LENGTH: 10
<212> TYPE: DNA
<213> ORGANISM: Artificial
<220> FEATURE:
<223> OTHER INFORMATION: Primer

<400> SEQUENCE: 15
gaatcggcca                                                              10
```

-continued

```
<210> SEQ ID NO 16
<211> LENGTH: 10
<212> TYPE: DNA
<213> ORGANISM: Artificial
<220> FEATURE:
<223> OTHER INFORMATION: Primer

<400> SEQUENCE: 16
ccgaacacgg                                                              10

<210> SEQ ID NO 17
<211> LENGTH: 10
<212> TYPE: DNA
<213> ORGANISM: Artificial
<220> FEATURE:
<223> OTHER INFORMATION: Primer

<400> SEQUENCE: 17
ctccatgggg                                                              10

<210> SEQ ID NO 18
<211> LENGTH: 10
<212> TYPE: DNA
<213> ORGANISM: Artificial
<220> FEATURE:
<223> OTHER INFORMATION: Primer

<400> SEQUENCE: 18
cctctcgaca                                                              10

<210> SEQ ID NO 19
<211> LENGTH: 10
<212> TYPE: DNA
<213> ORGANISM: Artificial
<220> FEATURE:
<223> OTHER INFORMATION: Primer

<400> SEQUENCE: 19
tgagcctcac                                                              10

<210> SEQ ID NO 20
<211> LENGTH: 10
<212> TYPE: DNA
<213> ORGANISM: Artificial
<220> FEATURE:
<223> OTHER INFORMATION: Primer

<400> SEQUENCE: 20
cattcgagcc                                                              10

<210> SEQ ID NO 21
<211> LENGTH: 10
<212> TYPE: DNA
<213> ORGANISM: Artificial
<220> FEATURE:
<223> OTHER INFORMATION: Primer

<400> SEQUENCE: 21
cacctttccc                                                              10

<210> SEQ ID NO 22
<211> LENGTH: 10
<212> TYPE: DNA
<213> ORGANISM: Artificial
<220> FEATURE:
<223> OTHER INFORMATION: Primer
```

```
<400> SEQUENCE: 22
gaacactggg                                                              10

<210> SEQ ID NO 23
<211> LENGTH: 10
<212> TYPE: DNA
<213> ORGANISM: Artificial
<220> FEATURE:
<223> OTHER INFORMATION: Primer

<400> SEQUENCE: 23
agcaggtgga                                                              10

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
aggtgcgatg tcgtccctca                                                   20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
tgggtgggat acttcgctgg                                                   20

<210> SEQ ID NO 26
<211> LENGTH: 15
<212> TYPE: DNA
<213> ORGANISM: Artificial
<220> FEATURE:
<223> OTHER INFORMATION: Primer

<400> SEQUENCE: 26
gtcccggtgt gacca                                                        15

<210> SEQ ID NO 27
<211> LENGTH: 15
<212> TYPE: DNA
<213> ORGANISM: Artificial
<220> FEATURE:
<223> OTHER INFORMATION: Primer

<400> SEQUENCE: 27
gccatgagcg atcat                                                        15

<210> SEQ ID NO 28
<211> LENGTH: 19
<212> TYPE: DNA
<213> ORGANISM: Artificial
<220> FEATURE:
<223> OTHER INFORMATION: Primer

<400> SEQUENCE: 28
ccttccaaga aacccact                                                     19

<210> SEQ ID NO 29
<211> LENGTH: 19
```

-continued

```
<212> TYPE: DNA
<213> ORGANISM: Artificial
<220> FEATURE:
<223> OTHER INFORMATION: Primer

<400> SEQUENCE: 29
atttccgaga tcaccgaga                                                19

<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
tggtcacaga aggtcctcag                                               20

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
cgcatacatt ccaagagcac                                               20
```